US011304722B2

(12) United States Patent
Eedarapalli et al.

(10) Patent No.: US 11,304,722 B2
(45) Date of Patent: Apr. 19, 2022

(54) DECLOGGING METHOD AND SYSTEM (71) Applicant: Gyrus ACMI, Inc., Southborough, MA (US)

(72) Inventors: Satyanarayana Raju Eedarapalli, Collierville, TN (US); Ahmad Alsaffar, Bartlett, TN (US); Kevin C. Edwards, Olive Branch, MS (US)

(73) Assignee: Gyrus Acmi, Inc., Westborough, MA (US)

( * ) Notice: Subject to any disclaimer, the term of this patent is extended or adjusted under 35 U.S.C. 154(b) by 328 days.

(21) Appl. No.: 16/267,775

(22) Filed: Feb. 5, 2019

(65) Prior Publication Data
US 2020/0246035 A1 Aug. 6, 2020

(51) Int. Cl.
*A61B 17/3205* (2006.01)
*A61B 17/00* (2006.01)

(52) U.S. Cl.
CPC .............. *A61B 17/3205* (2013.01); *A61B 2017/00477* (2013.01); *A61B 2017/00544* (2013.01); *A61B 2217/005* (2013.01)

(58) Field of Classification Search
CPC .......... A61B 17/32002; A61B 17/3205; A61B 2017/00477; A61B 2017/00544; A61B 2090/701; A61B 2217/005; A61B 90/70; A61M 1/74; A61M 2025/0019; A61M 2205/075
See application file for complete search history.

(56) References Cited

U.S. PATENT DOCUMENTS

| 2009/0087249 | A1* | 4/2009 | Flagle | A61B 10/0275 403/31 |
| 2010/0176584 | A1* | 7/2010 | Ito | A61M 39/10 285/23 |
| 2013/0289595 | A1* | 10/2013 | Edwards | A61B 17/32002 606/170 |

FOREIGN PATENT DOCUMENTS

| EP | 2161013 A1 | 3/2010 |
| WO | WO-2020163071 A1 | 8/2020 |

OTHER PUBLICATIONS

"International Application Serial No. PCT/US2020/014337, International Search Report dated May 7, 2020", 4 pgs.
"International Application Serial No. PCT/US2020/014337, Written Opinion dated May 7, 2020", 7 pgs.
"International Application Serial No. PCT/US2020/014337, International Preliminary Report on Patentability dated Aug. 19, 2021", 9 pgs.

* cited by examiner

*Primary Examiner* — Mohamed G Gabr
(74) *Attorney, Agent, or Firm* — Schwegman Lundberg & Woessner, P.A.

(57) ABSTRACT

A medical device includes a hollow tubular connector having a first open end and a second open end, the first open end configured to be connected to a suction port of a surgical cutting device, and the second open end configured to be connected to a source of pressurized air, the hollow tubular connector including a first seal located proximate the first open end and having a first diameter, the first seal being configured to sealingly accommodate a tubular shank, of a first diameter, of a blade of the surgical cutting device.

9 Claims, 11 Drawing Sheets

DECLOGGING METHOD AND SYSTEM

BACKGROUND

Field of the Invention

The exemplary and non-limiting embodiments described herein relate generally to devices and methods that relate to the clearing of obstructions from surgical instruments during surgical procedures. The exemplary and non-limiting embodiments described herein relate more particularly to pressure-operated declog mechanisms that facilitate the clearing of suction lines during use of a tissue debriding instrument.

Brief Description of Prior Developments

Debridement involves the controlled, surgical removal of damaged tissue from a wound to promote wound healing. Types of debridement techniques in current use include sharp, autolytic, chemical, mechanical, and biologic debridement. Sharp debridement techniques employ sharp devices hereinafter referred to as "debriders" that are used by surgeons to cut necrotic, infected, or otherwise damaged tissue away from healthy tissue. These debriders may be simple bladed instruments such as curettes or scalpels. More complex debriders may include ports in the blades and associated lines to supply fluid for wound irrigation and/or for suction to carry debrided tissue away from the wound during debridement procedures.

Debriders equipped with suction typically clog with debrided tissue when large amounts of the tissue are drawn up. Older debriders often required the use of a stylet to clear a clog. More up-to-date debriders generally use a manually-operated pressure bulb that, when squeezed, purges the clog back through the blade. Such mechanisms are generally known as "decloggers."

SUMMARY

In accordance with one aspect, a medical device comprises a hollow tubular connector having a first open end and a second open end, the first open end configured to be connected to a suction port of a surgical cutting device, and the second open end configured to be connected to a source of pressurized air, the hollow tubular connector comprising a first seal located proximate the first open end and having a first diameter, the first seal being configured to sealingly accommodate a tubular shank, of a first diameter, of a blade of the surgical cutting device.

In accordance with another aspect, a medical device comprises a squeeze bulb comprising a first end having an opening through which air is expelled upon squeezing of the squeeze bulb; and a hollow tubular connector having a first open end connected to the first open end of the squeeze bulb, and having a second open end configured to be connected to a suction port of a surgical cutting device. The squeeze bulb and the hollow tubular connector define a modular assembly that is connectable to the suction port to allow for a removal of an obstruction in the surgical cutting device.

In accordance with another aspect, a method of clearing an obstruction from a surgical cutting device comprises providing the surgical cutting device having a cutting assembly; providing a manually-operated squeeze bulb having a connector; connecting the surgical cutting device to the connector; and activating the squeeze bulb to pressurize the surgical cutting device to clear the obstruction.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
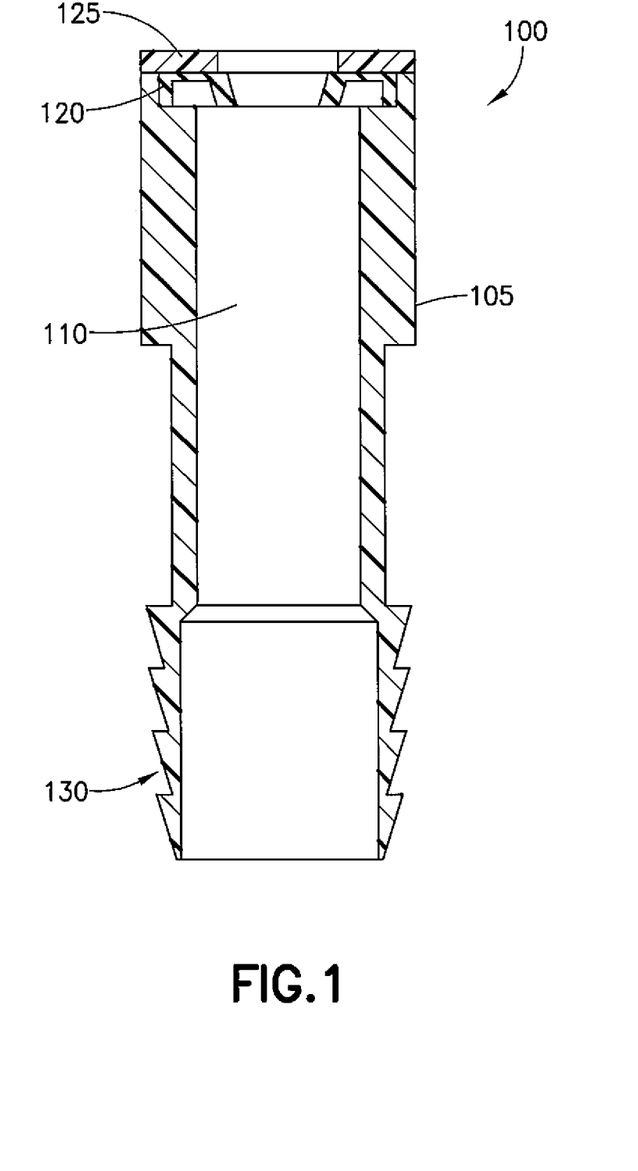
FIG. 1 is a side sectional view of one exemplary embodiment of a declog unit.

Referring to FIG. 1, one exemplary embodiment of a declog unit for use with a debrider or other bladed surgical cutting device is shown generally at 100. The declog unit 100 may be operated to apply pressure to purge obstructions of tissue, bone, and the like from the debrider. In any embodiment disclosed herein, at least the shank of the blade is tubular, and the blade may be disposable.

The declog unit 100 may, be a valve comprising a substantially cylindrical body 105 with a bore 110 extending longitudinally from a first open end in which an instrument is inserted and a second open end that is inserted into a pressure bulb. The first open end includes a suction seal 120 (adjustable, seal, sealing member, or the like) disposed circumferentially around the opening. The suction seal may be a circumferential rubber element such as an O-ring, QUAD-RING, U-cup seal, V-shaped seal, lip-type seal, or other element having a shape having an opening that corresponds with a circumferential shape of a portion of the instrument. The opening of the circumferential rubber element may be visible, or it may be closed as with a self-closing duck-bill or similar type of seal used in trocar assemblies. Other seal materials, shapes, and types are also possible. The instrument may be the shank of a blade, or a cannula, tube, or the like into which the shank of a blade is inserted.

The first open end also includes a seal holder 125 disposed on top of the suction seal 120, the seal holder 125 being a washer of substantially rigid material held on the first open end by snap fitting, ultrasonic welding, adhesive (such as glue), heat-staking, or the like to help maintain the suction seal 120 in place. The seal holder 125 has an opening extending therethrough, the opening being equal or larger in diameter than the opening extending through the suction seal 120 such that upon insertion of the blade shank (or other instrument), the suction seal 120 may (in some embodiments, such as with an O-ring) expand radially outward and, upon pressurizing the declog unit 100, be urged or held against an underside of the seal holder 125. The seal holder 125 may be of other designs, types, or materials as well. The second open end of the body 105 of the declog unit 100 may be configured as a barb connector 130 for insertion into the pressure bulb.

Figure 2A:
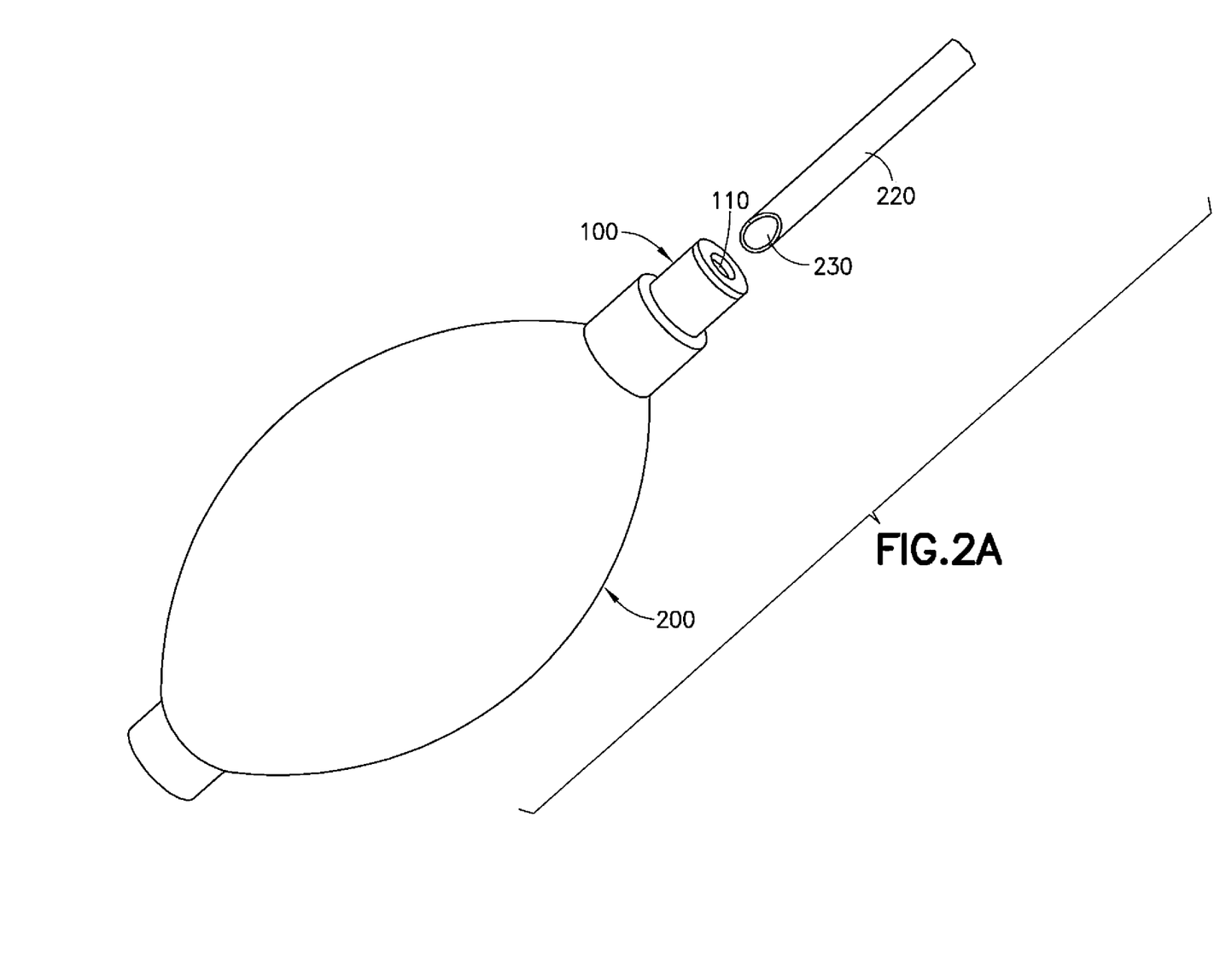
FIG. 2A is a perspective view of insertion of a blade into the declog unit of FIG. 1.

Referring to FIG. 2A, the barb connector 130 of the declog unit 100 is inserted into a manually-operated pressure bulb. 200 that is configured to expel air when squeezed by a user. As shown, the bore 110 of the declog unit 100 accommodates a blade 220 (or other instrument) of a specific size or a variable size, depending upon the type of seal, the distal end of the shank of the blade 220 being mounted in the suction seal 120 at the first open end of the body 105 of the declog unit 100. An open window 230 is located proximate the distal end of the blade 220.

Figure 2B:
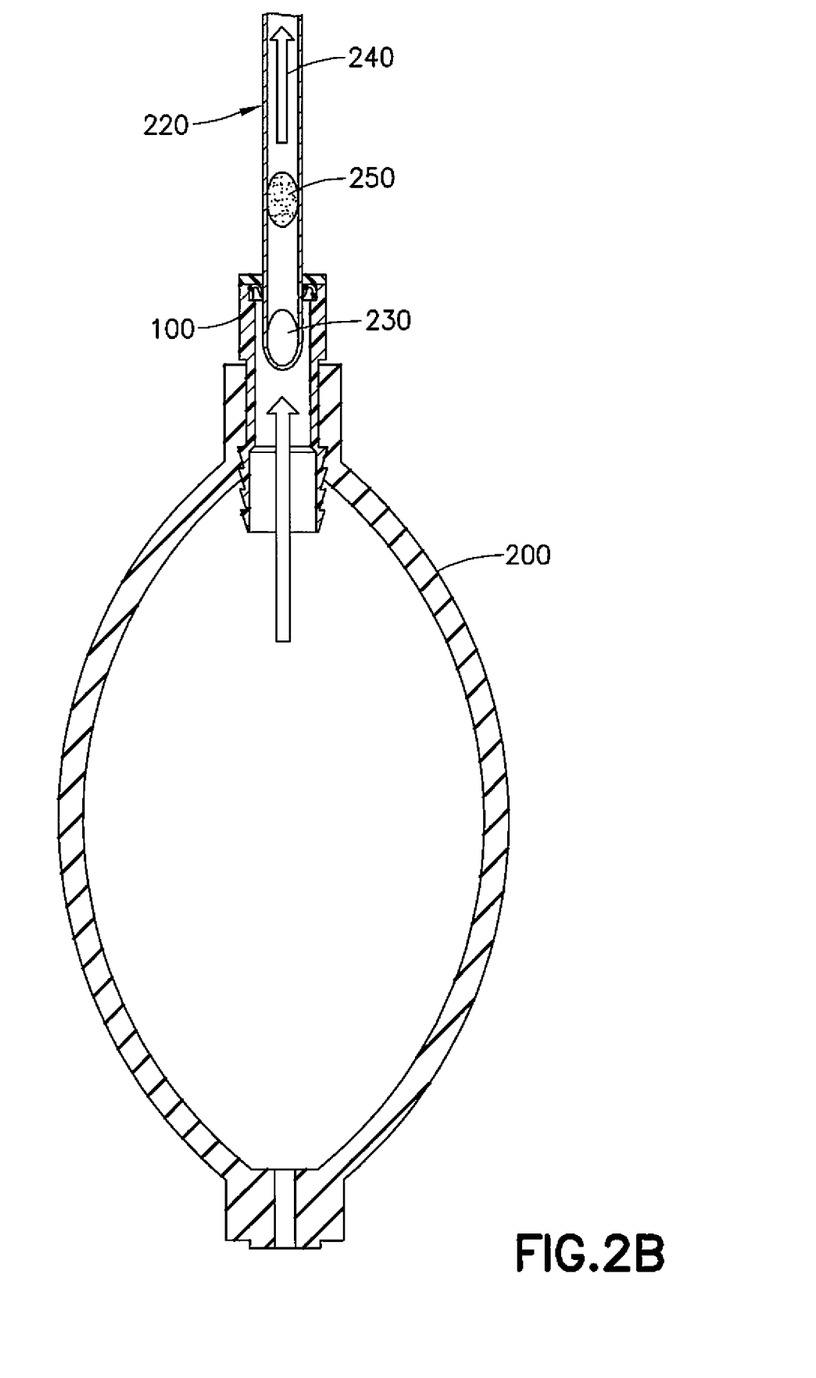
FIG. 2B is a side sectional view of the inserted blade of FIG. 2A.

Referring to FIG. 2B, when the shank of the blade 220 is inserted into the declog unit 100, the terminus of the shank is positioned intermediate the first and second open ends of the bore 110. When the pressure bulb 200 is operated by being squeezed by a user, air pressure is applied through the open window 230 to pressurize the inner shank of blade 220, thereby causing flow in the direction indicated by arrow 240, to purge any clogs 250 that may be lodged in the inner shank of the blade 220 or at a cutting portion of the blade 220.

Figure 3:
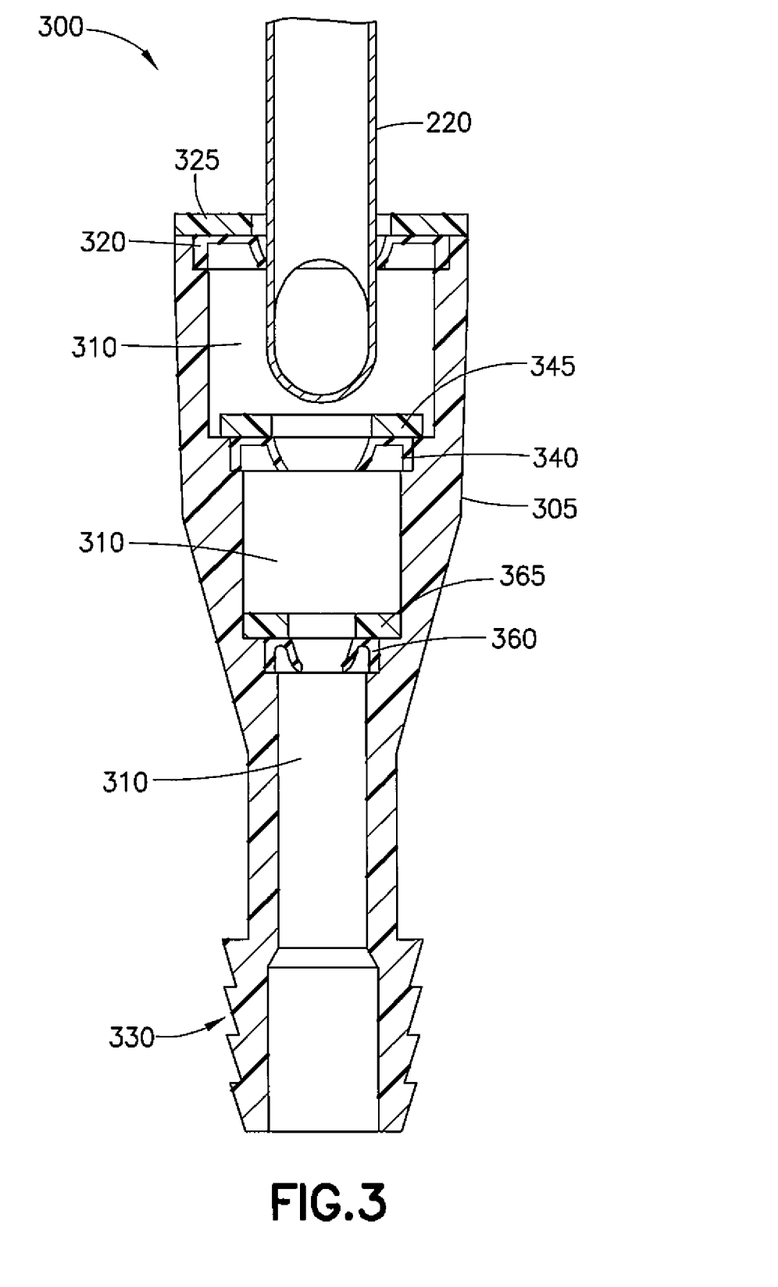
FIG. 3 is a side sectional view of another exemplary embodiment of a declog unit.

Referring to FIG. 3, another exemplary embodiment of a declog unit for use with a debrider or other bladed surgical device is shown generally at 300. The declog unit 300 comprises a substantially cylindrical body 305 having a bore 310 extending longitudinally from a first open end in which the shank of a blade 220 (or cannula, tube, or the like) is inserted toward a second open end that is inserted into the pressure bulb. The outer surface of the body 305 is tapered from the first open end to the second open end. The second open end of the body 305 may be configured as a barb connector 330 for insertion into the pressure bulb.

The body 305 includes suction seals and seal holders of various sizes mounted in the bore 310. More specifically, the first open end includes a first seal holder 325 disposed on top of the first suction seal 320 (adjustable seal, sealing member, or the like), the first seal holder 325 being a washer of substantially rigid material held on the first open end by snap fitting, ultrasonic welding, adhesive (such as glue), heat-staking, or the like to maintain the first suction seal 320 in place.

A second seal holder 345 and a second suction seal 340 are configured similar to the first seal holder 325 and the first suction seal 320 and are positioned intermediate opposing open ends of the bore 310, but they are of smaller diameters in order to be mounted in a narrower section of the body 305. Additionally, the third seal holder 365 and the third suction seal 360 are configured similar to the other seal holders and the other suction seals, but they are of even smaller diameters in order to be mounted in a still narrower section of the body 305.

Figure 4A:
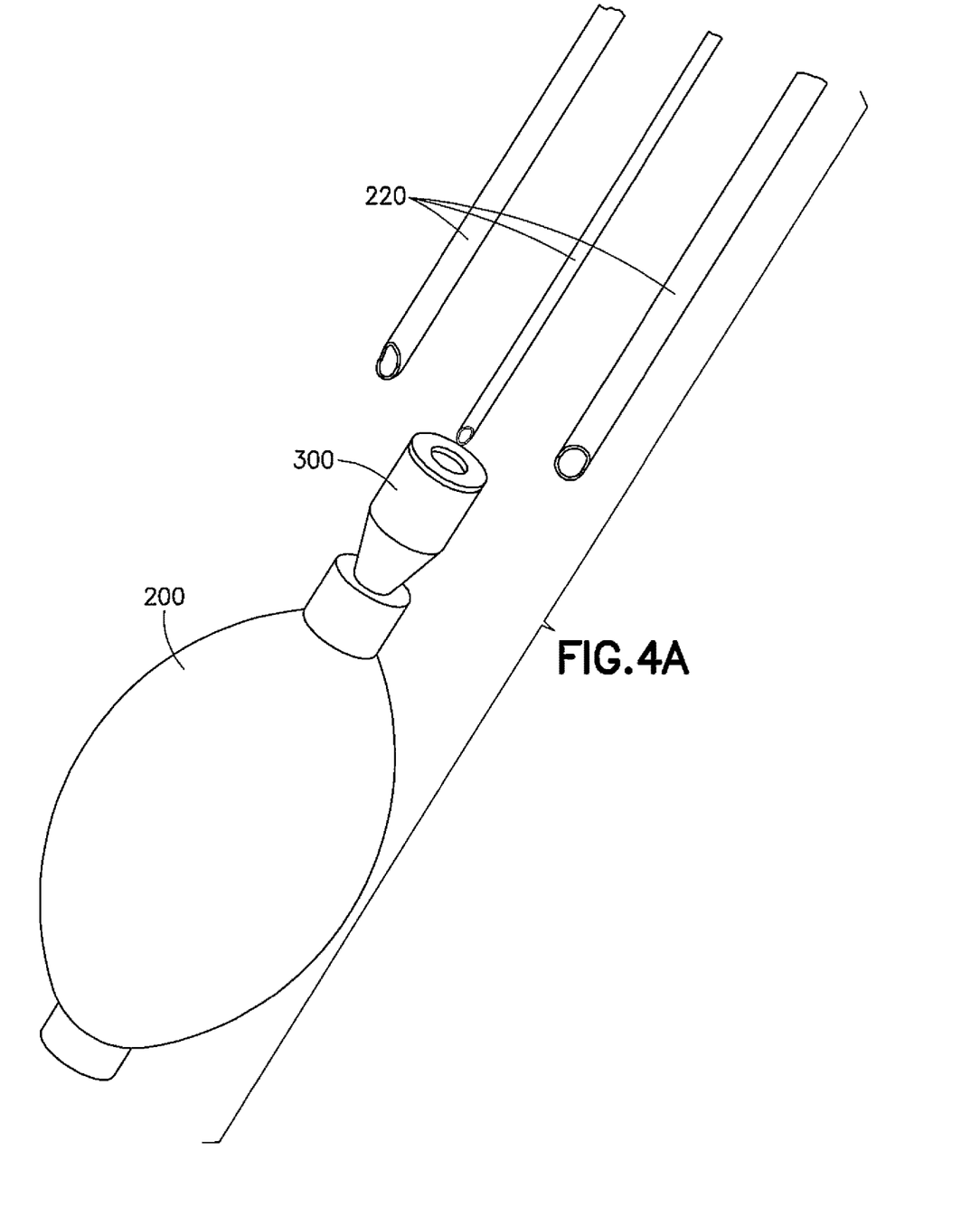
FIG. 4A is a perspective view of insertion of a blade into the declog unit of FIG. 3.

Referring to FIG. 4A, the barb connector 330 of the declog unit 300 is inserted into a pressure bulb 200. The bore 310 of the declog unit 300 accommodates the shanks of blades 220 (or cannula, tube, or the like) of different sizes, the distal end of a shank being inserted into the first open end of the body 305.

Figure 4B:
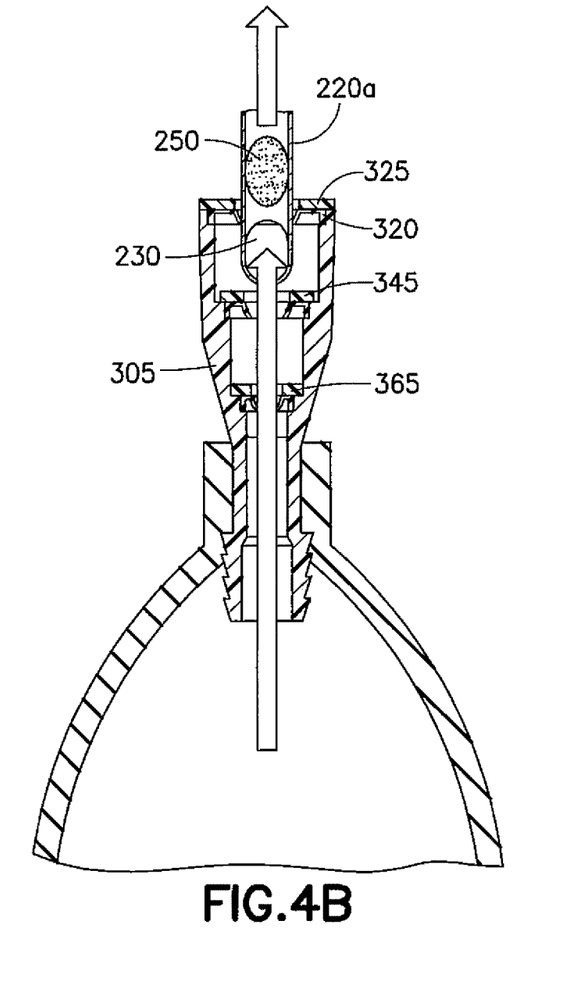
FIGS. 4B through 4D are side sectional views of various inserted blades of FIG. 4A.
Figure 4C:
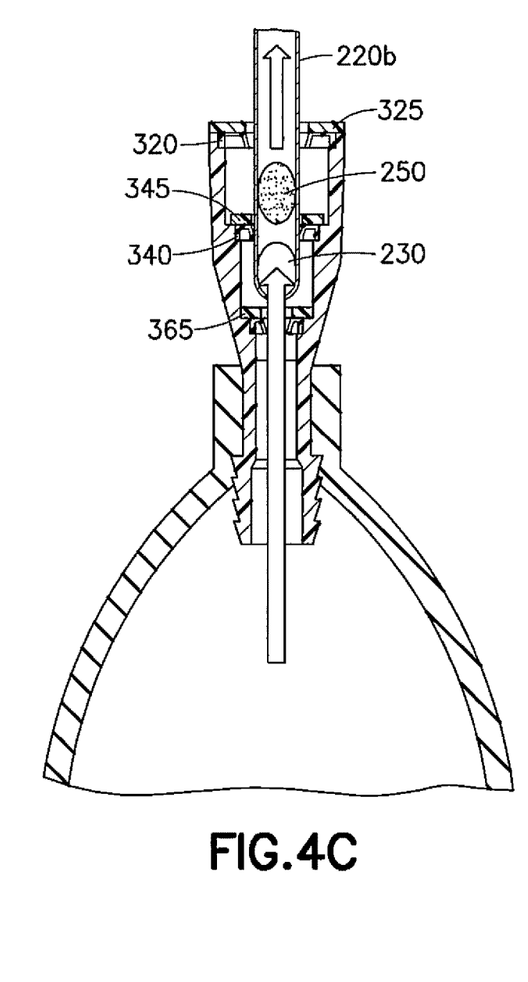
Figure 4D:
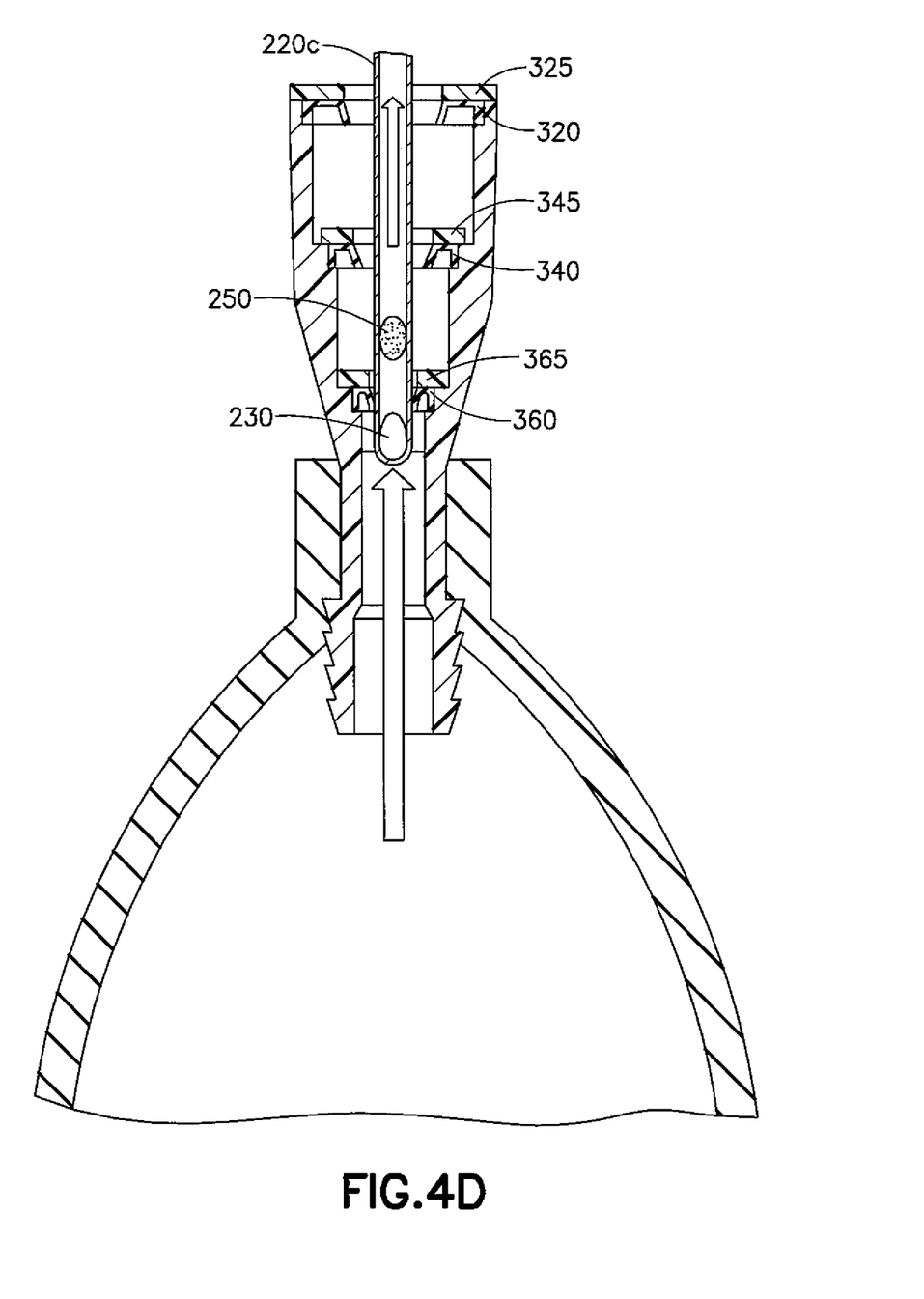

Referring to FIG. 4B, when a larger blade 220*a* is inserted in the first seal holder 325 and first suction seal 320, the terminus of the shank of the blade 220*a* is positioned forward of the second seal holder 345. Similarly, as shown in FIG. 4C, when a medium sized blade 220*b* is inserted, the shank thereof extends through the first seal holder 325 and the first suction seal 320 as well as the second seal holder 345 and second suction seal 340, and the terminus of the shank of the blade 220*b* is positioned forward of the third seal holder 365. Likewise, as shown in FIG. 4D, when a small blade 220*c* configured to be accommodated in the third seal holder 365 and third suction seal 360 is inserted, the terminus of the shank of the blade 220*c* is pushed through the third suction seal 360 and positioned forward of the second open end of the body 305. When any size blade is inserted into the body 305, when the pressure bulb 200 is operated by being squeezed by a user, air pressure is applied through an open window 230 located proximate the distal end of the blade 220 to purge any clogs 250 that may be lodged anywhere in the blade 220. As stated above, in any embodiment, the device accommodated in the declog unit may be a blade shank, or a cannula, tube, or the like.

As shown, the first seal holder 325 and the first suction seal 320 are configured to accommodate the shank of a blade 220 of a first size, for example, blade sizes from about 4.6 millimeters (mm) to about 7 mm. The second seal holder 345 and the second suction seal 340 are configured to accommodate the shank of a blade of a second size, for example, blade sizes from about 3.1 mm to about 4.5 mm. The third seal holder 365 and the third suction seal 360 are configured to accommodate the shank of a blade of a third size, for example, blade sizes from about 2 mm to about 3 mm.

Figure 5:
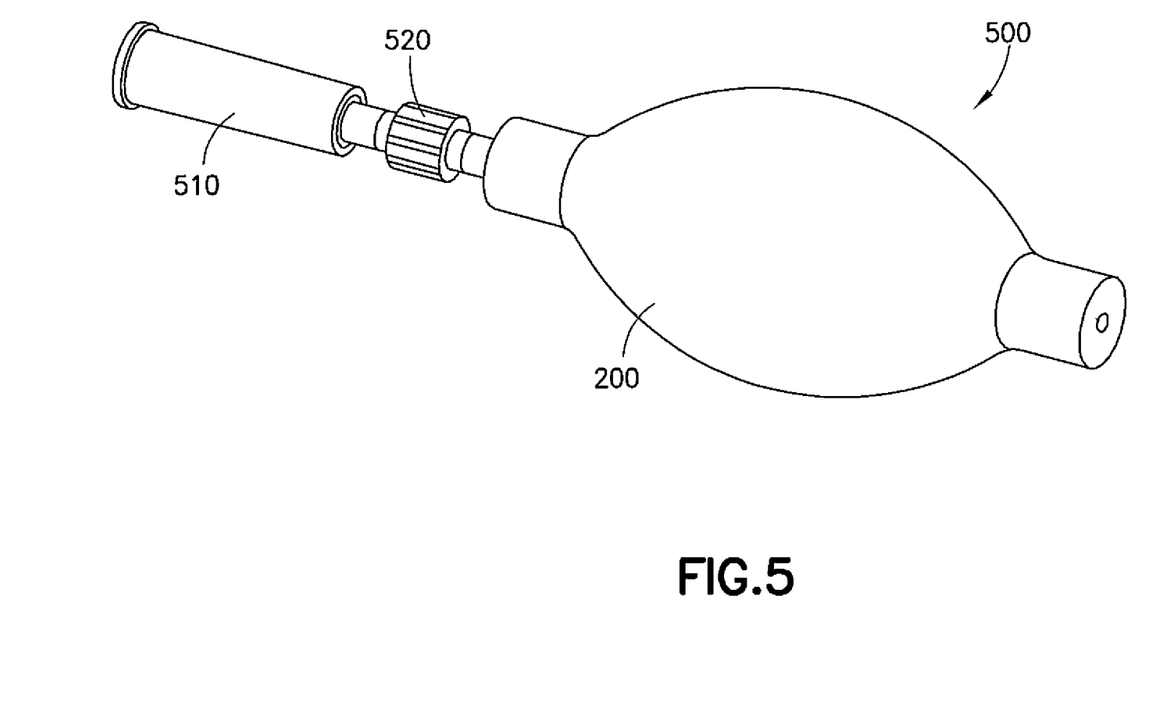
FIG. 5 is a perspective view of a modular declog unit.

Referring to FIG. 5, in debrider systems that employ suction, one exemplary embodiment of a modular declog unit is shown generally at 500 and is hereinafter referred to as "modular declog unit 500." The modular declog unit 500 comprises a connection port 510 and a manually-operated pressure bulb 200 coupled to the connection port 510. A check valve 520 may be located in-line between the connection port 510 and the pressure bulb 200. The modular declog unit 500 can be integrated in-line to debrider handpieces that utilize a universal/barbed connection for suction tubing. In some systems, the pressure bulb 200 can be directly coupled to the distal end of the blade 220 when a clog is detected.

Figure 6A:
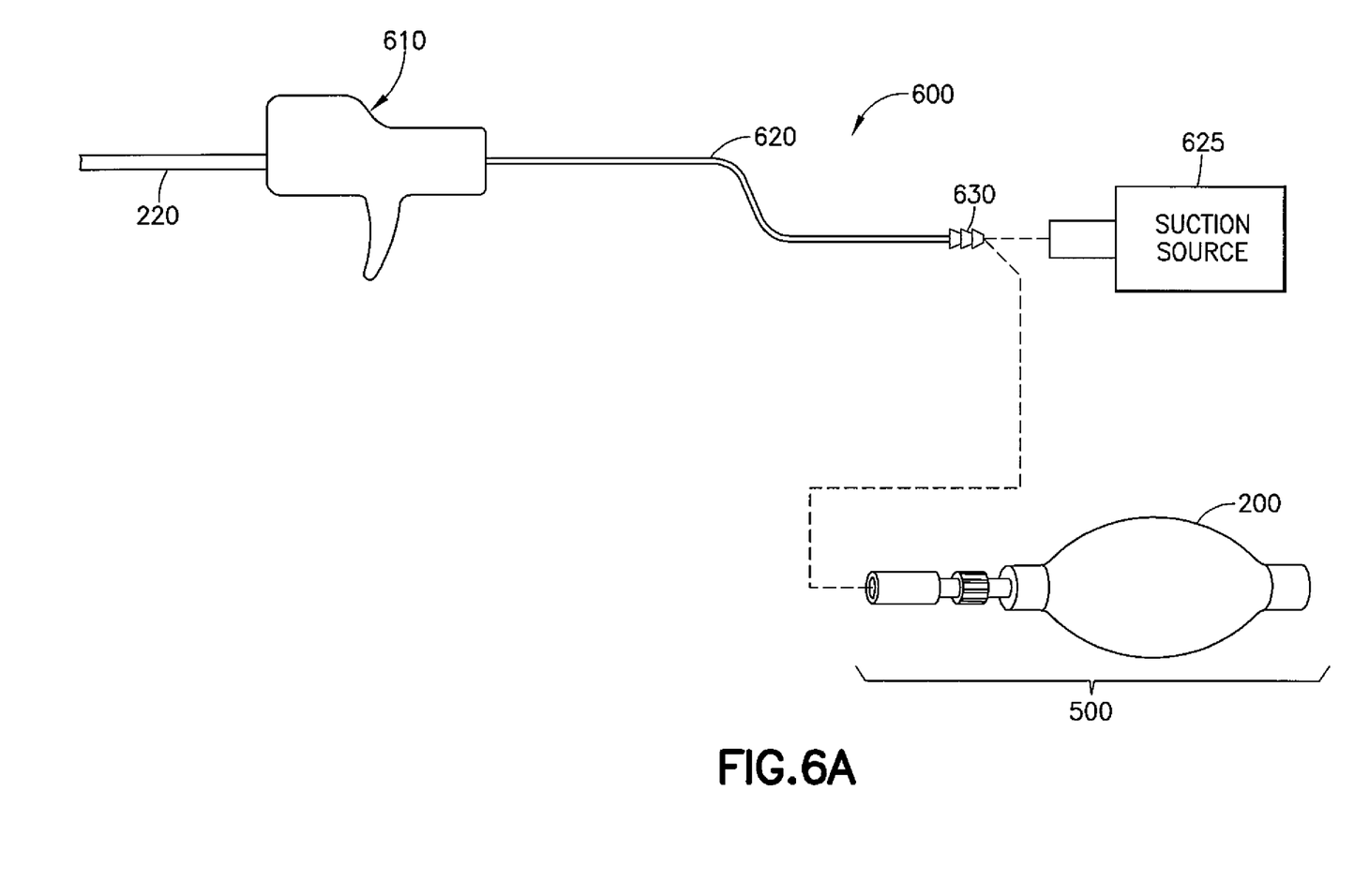
FIGS. 6A and 6B are schematic representations of exemplary embodiments of systems using the modular declog unit of FIG. 5.

Referring to FIG. 6A, in one configuration of a system 600 for the intermittent use of the modular declog unit 500 with a debrider 610, suction tubing 620 extending from the debrider 610 can be disconnected from a suction source 625 and coupled to the modular declog unit 500 when a clog is detected. In particular, when the suction tubing. 620 extending from the debrider 610 terminates in a barbed connector 630, the barbed connector 630 can be detached from the suction source 625 (or an in-line connector that is coupled to the suction source 625) and inserted into the modular declog unit 500. Upon operation of the modular declog unit 500 and clearing of the clog, the barbed connector 630 can be decoupled from the modular declog unit 500 and reconnected to the suction source 625 (or in-line connector) to resume normal operation.

Figure 6B:
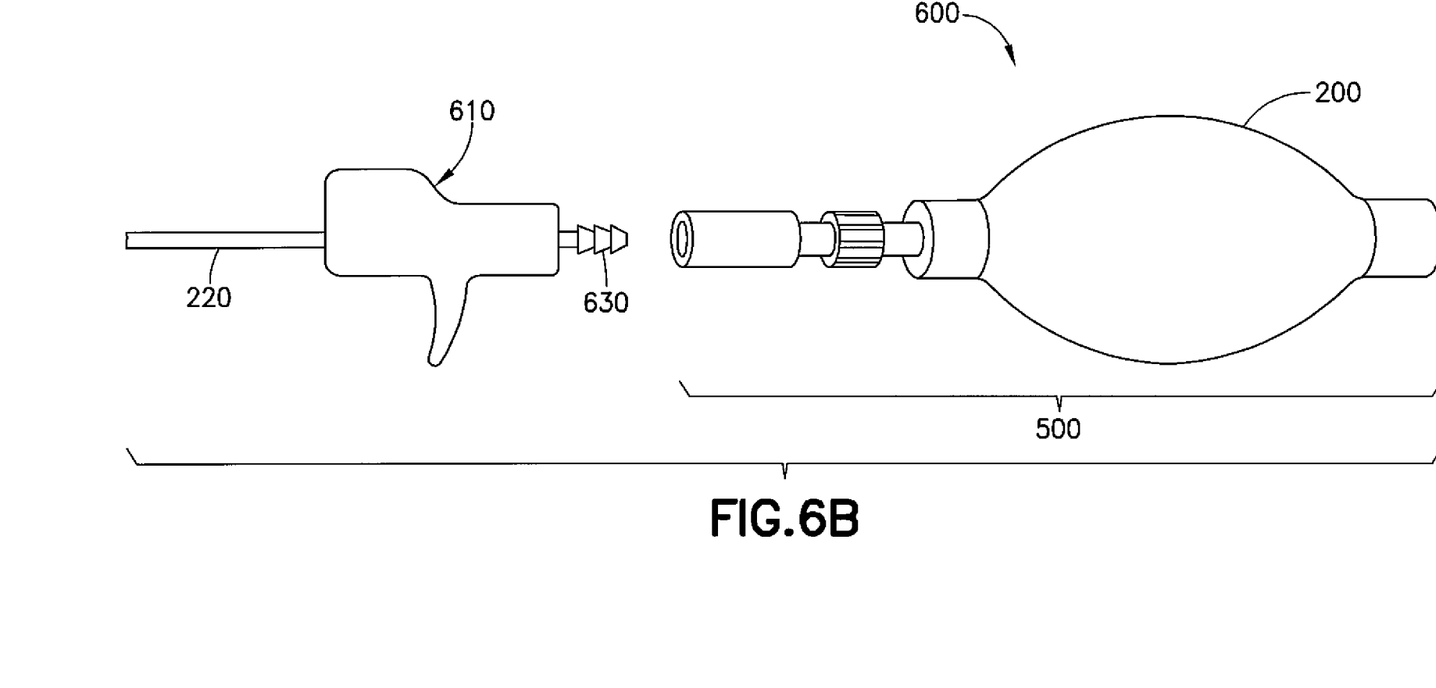

Referring to FIG. 6B, in another configuration of a system 600 for the intermittent use of the modular declog unit 500, the modular declog unit 500 may be directly connected to a barbed connector 630 at the debrider 610. More specifically, the modular declog unit 500 can be directly connected to the debrider 610 without the suction tubing 620. Thus, the suction tubing 620 is optional in the embodiment of FIG. 6B.

Figure 7:
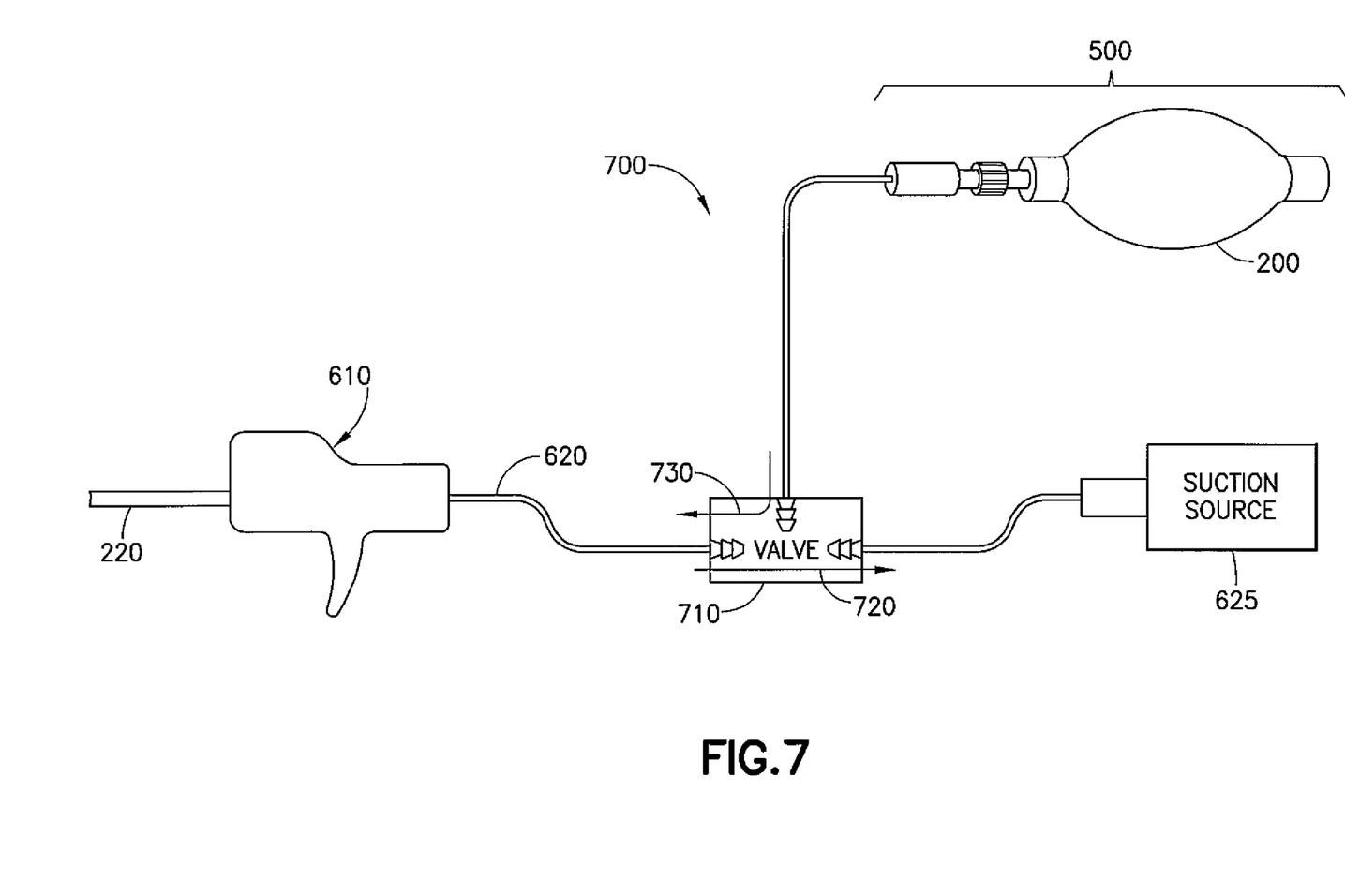
FIG. 7 is a schematic representation another exemplary embodiment of a system using the modular declog unit of FIG. 5.

Referring to FIG. 7, in another configuration of a system 700 of using the modular declog unit 500 with a debrider 610, the modular declog unit 500 can be semi-permanently coupled to the debrider 610 by being removably coupled to a 3-way 2-position valve 710, which may be coupled to the debrider 610 through suction tubing 620 as shown, or which may be coupled directly to the debrider 610 (making suction tubing 620 optional). In another configuration, the modular declog unit 500 can be fixedly pre-attached to the valve 710. In any configuration, the valve 710 is generally configured to toggle between a "declog mode" when a clog is detected and normal operation when no clog is present. The valve is further configured to allow suction (arrow 720) when the pressure bulb 200 of the modular declog unit 500 is not operated or when the valve is in a first or "1" position. When the pressure bulb 200 is operated or when the valve is in a second or "2" position, the suction is interrupted and air flows from the pressure bulb 200 through the valve 710 and to the debrider 610 (arrow 730), thereby allowing for the clearing of a clog at the debrider 610.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described below, may be implemented, practiced, or utilized in any combination (for example, any combination that is suitable, practicable, and/or feasible) and are not limited only to those combinations described herein and/or included in the appended claims.

In one exemplary embodiment, a medical device comprises a hollow tubular connector having a first open end and a second open end, the first open end configured to be connected to a suction port of a surgical cutting device, and the second open end configured to be connected to a source of pressurized air, the hollow tubular connector comprising a first seal located proximate the first open end and having a first diameter, the first seal being configured to sealingly accommodate a tubular shank, of a first diameter, of a blade of the surgical cutting device.

The medical device may further comprise a second seal located proximate the second open end and having a second diameter that is less than the first diameter, the second seal being configured to sealingly accommodate a tubular shank, of a second diameter that is less than the first diameter, of a blade of the surgical cutting device. If the tubular shank of the first diameter of the blade of the surgical cutting device is inserted, a terminus of the tubular shank extends through the first suction seal and does not extend to the second suction seal, and if the tubular shank of the second diameter of the blade of the surgical cutting device is inserted, a terminus of the tubular shank extends through the first suction seal and through the second suction seal. The medical device may further comprise at least one third seal located in the hollow tubular connector intermediate the first seal and the second seal, the third seal being configured to sealingly accommodate a tubular shank, of a third diameter that is less than the first diameter of the blade of the surgical cutting device and greater than the second diameter of the blade of the surgical cutting device. The medical device may further comprise a first seal holder on the first seal, the first seal holder configured to maintain the first seal in place. The first seal holder may be at least one of snap fitted, ultrasonically welded, adhesively coupled, or heat-staked to the hollow tubular connector. The second open end of the body may be configured as a barbed connector. The source of pressurized air may be a manually-operated pressure bulb. The hollow tubular connector may comprise a gradually decreasing outer diameter from the first open end to the second open end. The seal may be a self-closing seal.

In another exemplary embodiment, a medical device comprises a squeeze bulb comprising a first end having an opening through which air is expelled upon squeezing of the squeeze bulb; and a hollow tubular connector having a first open end connected to the first open end of the squeeze bulb, and having a second open end configured to be connected to a suction port of a surgical cutting device. The squeeze bulb and the hollow tubular connector define a modular assembly that is connectable to the suction port to allow for a removal of an obstruction in the surgical cutting device. The modular assembly may be connectable to the suction port through a valve.

In another exemplary embodiment, a method of clearing an obstruction from a surgical cutting device comprises providing the surgical cutting device having a cutting assembly; providing a manually-operated squeeze bulb having a connector; connecting the surgical cutting device to the connector; and activating the squeeze bulb to pressurize the surgical cutting device to clear the obstruction.

Connecting the surgical cutting device to the connector may comprise inserting a portion of the surgical cutting device through a self-closing seal in the connector. Inserting a portion of the surgical cutting device through the self-closing seal in the connector may comprise inserting a tubular shank of a blade of the surgical cutting device through the self-closing seal. Connecting the surgical cutting device to the connector may comprise detaching a suction line from the surgical cutting device and connecting the connector on the manually-operated squeeze bulb to the surgical cutting device. Connecting the surgical cutting device to the connector may comprise connecting the surgical cutting device to a valve and connecting the connector to the valve. Activating the squeeze bulb to pressurize the surgical cutting device may comprise closing a port in the valve and interrupting a suction applied to the surgical cutting device and pressurizing the surgical cutting device.

It should be understood that the foregoing description is only illustrative of the invention. Various alternatives and modifications can be devised by those skilled in the art without departing from the invention. Accordingly, the invention is intended to embrace all such alternatives, modifications, and variances which fall within the scope of the appended claims.

What is claimed is:

1. A medical device, comprising:
a hollow tubular connector having a first open end and a second open end, the first open end configured to be connected to a suction port of a surgical cutting device, and the second open end configured to be connected to a source of pressurized air;
a first seal located proximate the first open end and having a first diameter, the first seal being configured to sealingly accommodate a tubular shank, of a first diameter, of a blade of the surgical cutting device; and
a first seal holder on the first seal, the first seal holder configured to maintain the first seal in place;
wherein the second open end of the body is configured as a barbed connector.

2. The medical device of claim 1, further comprising a second seal located proximate the second open end and having a second diameter that is less than the first diameter, the second seal being configured to sealingly accommodate a tubular shank, of a second diameter that is less than the first diameter, of a blade of the surgical cutting device;
wherein if the tubular shank of the first diameter of the blade of the surgical cutting device is inserted, a terminus of the tubular shank extends through the first suction seal and does not extend to the second suction seal, and if the tubular shank of the second diameter of the blade of the surgical cutting device is inserted, a terminus of the tubular shank extends through the first suction seal and through the second suction seal.

3. The medical device of claim 2, further comprising at least one third seal located in the hollow tubular connector intermediate the first seal and the second seal, the third seal being configured to sealingly accommodate a tubular shank, of a third diameter that is less than the first diameter of the blade of the surgical cutting device and greater than the second diameter of the blade of the surgical cutting device.

4. The medical device of claim 1, wherein the first seal holder is at least one of snap fitted, ultrasonically welded, adhesively coupled, or heat-staked to the hollow tubular connector.

5. The medical device of claim 1, wherein the source of pressurized air is a manually-operated pressure bulb.

6. The medical device of claim 1, wherein the hollow tubular connector comprises a gradually decreasing outer diameter from the first open end to the second open end.

7. The medical device of claim 1, wherein the seal is a self-closing seal.

8. A medical device, comprising:
a squeeze bulb comprising a first end having an opening through which air is expelled upon squeezing of the squeeze bulb; and
a hollow tubular connector having a first open end connected to and in contact with the first open end of the squeeze bulb in an in-line configuration, and having a second open end configured to be connected to a suction port of a surgical cutting device;
wherein the squeeze bulb and the hollow tubular connector define a modular assembly that is connectable to the suction port to allow for a removal of an obstruction in the surgical cutting device.

9. The medical device of claim 8, wherein the modular assembly is connectable to the suction port through a valve.

* * * * *